(12) United States Patent
Wuest et al.

(10) Patent No.: US 9,155,810 B2
(45) Date of Patent: Oct. 13, 2015

(54) METHOD FOR MANUFACTURING A GASEOUS MIXTURE FOR TREATING POLLUTED ATMOSPHERES, DEVICE FOR IMPLEMENTING SAME, AND USE THEREOF

(75) Inventors: Robert Wuest, Rosheim (FR); Miroslav Vasko, Rosheim (FR)

(73) Assignee: AIR & D SOCIETE A RESPONSABILITE LIMITEE, Rosheim (FR)

( * ) Notice: Subject to any disclaimer, the term of this patent is extended or adjusted under 35 U.S.C. 154(b) by 64 days.

(21) Appl. No.: 14/000,254

(22) PCT Filed: Feb. 17, 2012

(86) PCT No.: PCT/FR2012/050343
§ 371 (c)(1),
(2), (4) Date: Sep. 11, 2013

(87) PCT Pub. No.: WO2012/110750
PCT Pub. Date: Aug. 23, 2012

(65) Prior Publication Data
US 2013/0343951 A1    Dec. 26, 2013

(30) Foreign Application Priority Data
Feb. 17, 2011  (FR) .................................... 11 51317

(51) Int. Cl.
| *A61L 9/015* | (2006.01) |
| *A61L 9/03* | (2006.01) |
| *A61L 9/12* | (2006.01) |
| *F24F 3/16* | (2006.01) |
| *A01M 13/00* | (2006.01) |

(52) U.S. Cl.
CPC ................ *A61L 9/015* (2013.01); *A01M 13/00* (2013.01); *A61L 9/032* (2013.01); *A61L 9/122* (2013.01); *F24F 3/16* (2013.01); *A61L 2209/134* (2013.01); *F24F 2003/1689* (2013.01)

(58) Field of Classification Search
CPC .................................... A61L 9/03; A61L 9/12
USPC ......................................... 422/4, 124; 96/222
See application file for complete search history.

(56) References Cited

U.S. PATENT DOCUMENTS

2008/0233001 A1    9/2008    Ricciardi et al.

FOREIGN PATENT DOCUMENTS

| EP | 1 334 735 | 8/2003 |
| EP | 1 593 397 | 11/2005 |
| EP | 2 071 947 | 6/2009 |
| WO | 02/25180 | 3/2002 |
| WO | 2004/030708 | 4/2004 |
| WO | 2005/092400 | 10/2005 |

OTHER PUBLICATIONS

International Search Report dated May 22, 2012, corresponding to PCT/FR2012/050343.

*Primary Examiner* — Sean E Conley
(74) *Attorney, Agent, or Firm* — Young & Thompson (57) ABSTRACT

The present disclosure relates to the field of treating atmospheres that are laden with substances that are nauseating and/or detrimental to human or animal health, specifically to the field of deodorising, perfuming, and/or purifying air at industrial or private sites. For this purpose, there is disclosed a method for enriching, preferably saturating, ordinary atmospheric air with active substances present in the gas phase, to a device for implementing the method, and to the use of the method for the treatment of polluted atmospheres. The method is especially characterized in that it advantageously includes a step of reinjecting a portion of the enriched gaseous mixture (MG) into an enrichment or saturation chamber (7) in order to increase the enrichment rate of the gaseous mixture (MG) or to maintain the mixture at the maximum saturation level thereof.

20 Claims, 3 Drawing Sheets

METHOD FOR MANUFACTURING A GASEOUS MIXTURE FOR TREATING POLLUTED ATMOSPHERES, DEVICE FOR IMPLEMENTING SAME, AND USE THEREOF

This invention relates to the field of treating foul-smelling atmospheres, in particular atmospheres laden with substances that are nauseating and/or detrimental to human or animal health, and it relates more particularly to the deodorizing, the perfuming, the purifying (for example, disinfection) and/or insect control of air as can be present on industrial or private sites. For this purpose, it has as its object a method for enriching, preferably saturating, ordinary atmospheric air with active substances that are present in the gaseous phase, in particular with volatile substances for deodorizing, perfuming, disinfecting and/or insect control, a device for implementing said method and the use of said method for treating polluted air. Actually, such an enriched or saturated gas mixture will then make it possible to treat a polluted atmosphere effectively by deodorizing it, perfuming it by making it clean and/or safe (free of pollutants, pathogenic agents or disease-carrying or annoying insects) for individuals who breathe it.

Methods and devices designed to create a gas mixture based on ordinary atmospheric air containing substances or active ingredients for deodorizing, perfuming and/or purifying ambient air are known.

The application EP 1 593 397 A1 describes a column-shaped device comprising a gel in which active substances circulating in an upward air stream created by a fan located at the base of said column are adsorbed.

The application EP 2 071 947 A1 proposes a device and method of these types, in which the healthy ordinary air is breathed in from the environment and then brought into contact with active substances at constant atmospheric pressure, with the amount of drawn-off air corresponding, at any moment, to the amount of air laden with active substances exiting from said device to be sent to the sites where it is used to treat the polluted air.

These devices do not, however, provide optimal results to the extent that said volatile active substances are only very partially entrained under the action of the single passage of the stream of fresh air created for this purpose. The air that exits from these devices is therefore only relatively lightly laden with active substances and therefore only slightly effective, and said devices thus have little or no ability to treat large volumes or volumes of heavily polluted air.

The purpose of this invention is to remedy the above-mentioned drawbacks.

For this purpose, it has as its object a method for enriching, preferably saturating, ordinary air with active substances that are present in the gaseous phase, in particular with volatile substances for deodorizing, perfuming, disinfecting and/or insect control, characterized in that it essentially consists in performing, in an essentially airtight chamber, the following operations:

a) Introducing gaseous fresh air that is not laden with active substances into said chamber, b) Introducing it via at least one inlet into at least one enrichment or saturation chamber, for bringing said fresh air into contact with at least one volatile active substance that is present in the gaseous phase so as to enrich it, preferably until it is saturated, with said volatile active substance(s), c) Drawing off, at the outlet of said enrichment or saturation chamber(s), a portion of the enriched gas mixture at a level that is sufficient or saturated at the end of stage b) for the purpose of its storage in an internal storage chamber or its draining toward the outside via one or more outlet openings of said chamber, d) Reinjecting the portion of the gas mixture that is not drawn off at stage c) or all of said enriched gas mixture into said at least one enrichment or saturation chamber so as to increase the enrichment level of said gas mixture, keeping it at its maximum saturation level or reducing the saturation by mixing it, in this case, before the introduction into said at least one enrichment or saturation chamber with new non-laden fresh air introduced from the outside into said chamber.

According to an advantageous characteristic, the method according to this invention is characterized in that the gaseous fresh air that is not laden with active substances is introduced into said chamber by suction, preferably by being filtered, by means of at least one first suction device, preferably by means of a first fan at at least one inlet opening of said chamber.

Advantageously, the temperature of the incoming non-laden fresh air and/or the temperature of the gas mixture is adjusted by means of a heating and regulating device, and preferably maintained at approximately 25° C.

According to another characteristic, the bringing into gaseous contact, in at least one enrichment or saturation chamber, of said gaseous fresh air with said at least one volatile active substance in the gaseous phase so as to enrich said fresh air, preferably until it is saturated, in said volatile active substance(s) in gaseous phase, is done by making said fresh air or the reinjected gas mixture of stage d) circulate in, under and/or along one or more laden surfaces and/or through one or more volumetric bodies that are laden with one or more volatile active substances for deodorizing, perfuming, disinfecting and/or insect control and that thus circulate, in gaseous form, for enriching or saturating said fresh air or the reinjected gas mixture.

In a preferred way, said surface(s) and/or said volumetric body(ies) is/are heated directly or indirectly in an adjustable way by means of an adjustable heating device so as to regulate the amount of volatile active substance that is circulated or drawn off per unit of time and surface area.

Advantageously, the drawing-off at the at least one outlet of said enrichment or saturation chamber(s) of a portion of enriched gas mixture is done by suction by means of one or more suction devices, preferably by means of one or more compressors.

In an advantageous manner, the drawing-off at stage c) is done when the enrichment of the gas mixture in the active substance in the gaseous phase in question is greater than or equal to 50%, preferably greater than or equal to 70%, and more preferably greater than or equal to 95% of the theoretical maximum level of saturation of the air in said active substance.

According to another characteristic, the ratio between the incoming non-laden gaseous fresh air stream and the stream or streams of enriched or saturated gas mixture exiting from the chamber is greater than 1.5, preferably between 1.5 and 4, and more preferably between 4 and 8.

In a particularly practical manner, the reinjection of stage d) of the gas mixture that is enriched or saturated with new non-laden gaseous fresh air is done by means of at least one second suction device, preferably by means of a second fan.

Another advantageous aspect resides in the fact that the method according to the invention is characterized in that the gas stream generated by the at least first and/or second suction device, preferably the first and/or second fan, is regulated so as to control the amount of volatile active substance that is circulated or drawn off per unit of time and surface area.

According to another variant, the introduction of non-laden gaseous fresh air is done continuously during the entire enrichment or saturation cycle.

Advantageously, the amount and/or the time of introduction of non-laden gaseous fresh air and/or of drawing off the enriched or saturated gas mixture is/are programmable.

This invention also has as its object a device for implementing the method according to the invention, characterized in that it essentially comprises an essentially airtight chamber, equipped with at least one inlet opening and at least one outlet opening linking both with the outside of said chamber, a main compartment that is supplied—at a first zone of the latter—via said at least one opening with outside fresh air that is not laden with active substances by means of at least one first suction device, preferably at least one first fan, and equipped, within itself, with at least one second suction device, preferably at least one second fan that draws in the gases that are contained in said main compartment to at least one inlet of at least one enrichment or saturation chamber of said gases in volatile active substances, with the outlet(s) of the enrichment or saturation chamber(s) emptying into a second zone of said main compartment that is geographically removed from said first zone and inlet opening(s) and that is equipped, within itself, with at least one compressor for drawing off at least a portion of enriched or saturated gas mixture that is formed, headed for an internal storage chamber, an external consumer or an external intermediate storage tank via the at least one outlet opening, with said second zone being in gaseous communication with said first zone in such a way as to make it possible to reinject the enriched or saturated gas mixture formed in the at least one enrichment or saturation chamber, if necessary with the non-laden fresh air entering through the inlet opening(s).

According to another characteristic, the device according to the invention is characterized in that it comprises at least one means for heating and regulating the temperature of the outside fresh air that is not laden with active substances and/or gases already present in the main compartment.

The device according to the invention is also characterized in that the enrichment or saturation chamber(s) comprise(s) at least one surface that is laden—and/or at least one volumetric body that is laden—with volatile active substance(s) for deodorizing, perfuming, disinfecting and/or insect control, in such a way as to be able to circulate, in gaseous form, for enriching or saturating said fresh air or the reinjected gas mixture.

According to a preferred embodiment, the enrichment or saturation chamber(s) is/are produced in the form of airtight containers with an overall elongated shape inside of which are placed the surface(s) that is/are laden—and/or the volumetric body(ies) that is/are laden—with active substance(s) distributed over essentially the entire longitudinal range of said containers, preferably on at least two parallel levels that are flat and offset from one another in terms of height.

According to another characteristic, the enrichment or saturation chamber(s) has/have baffles.

Advantageously, the device according to the invention is characterized in that the enrichment or saturation chamber(s) has/have adjustable heating means of the surface(s) laden—and/or of the body(ies) laden—with active substance(s).

In another advantageous variant, the device in accordance with this invention is characterized in that it has several second fans, with each being connected to an enrichment or saturation chamber that is specific thereto, each enrichment or saturation chamber having its own outlet emptying into or connected to said second zone equipped with at least one compressor for drawing off at least one portion of enriched or saturated gas mixture, and an element for control and management of said several second fans and said compressor(s).

Finally, the invention also has as its object the use of the method according to the invention, characterized in that the enriched or saturated gas mixture that is obtained by implementing said method is mixed, according to an effective amount, with the polluted air that is to be treated for deodorizing it, perfuming it, purifying it and/or removing from it insects that it contains.

The invention will be better understood owing to the description below, which relates to preferred embodiments, provided by way of non-limiting examples and explained with reference to the accompanying diagrammatic drawings, in which.

Figure 1:
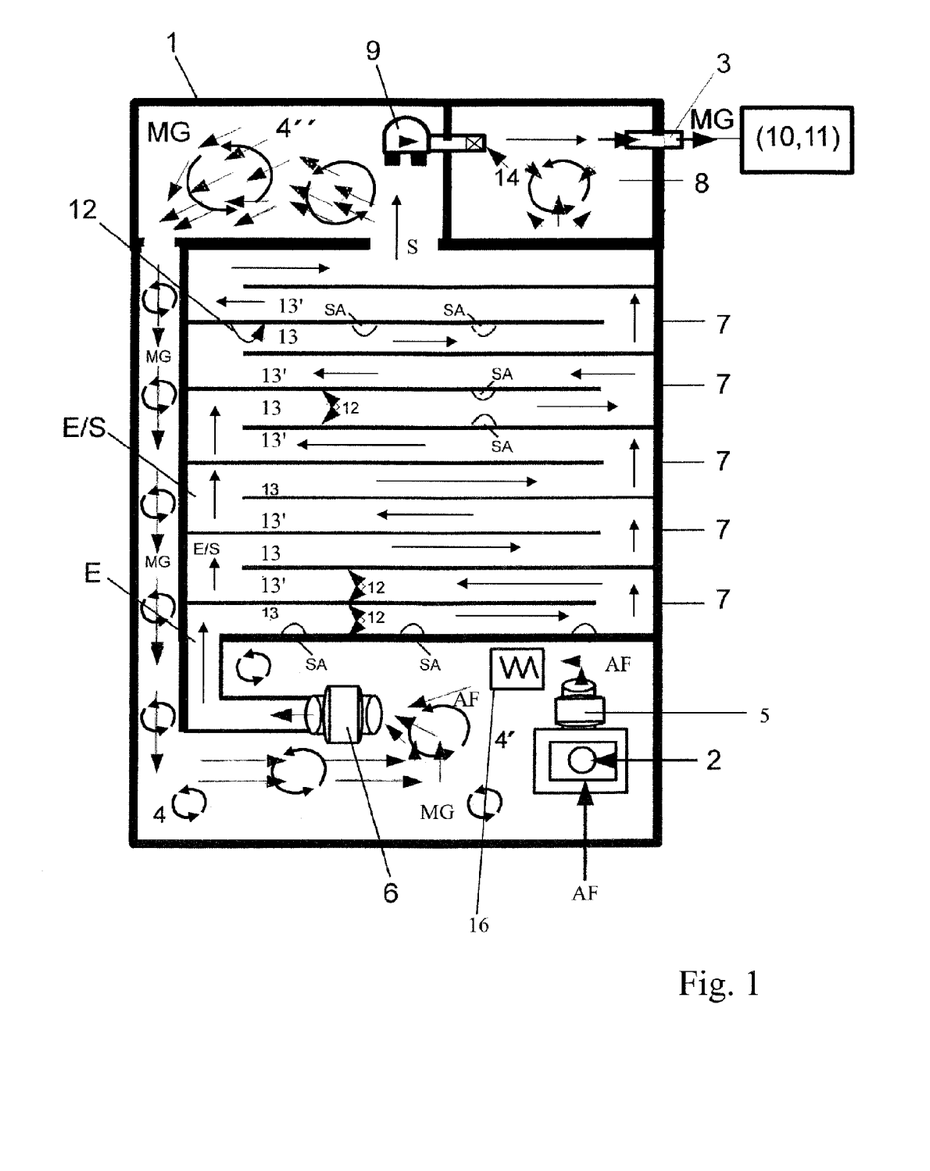
FIG. 1 shows, in a diagrammatic and simplified way, a side-elevation cutaway of a first embodiment of a device according to the invention.
Figure 2:
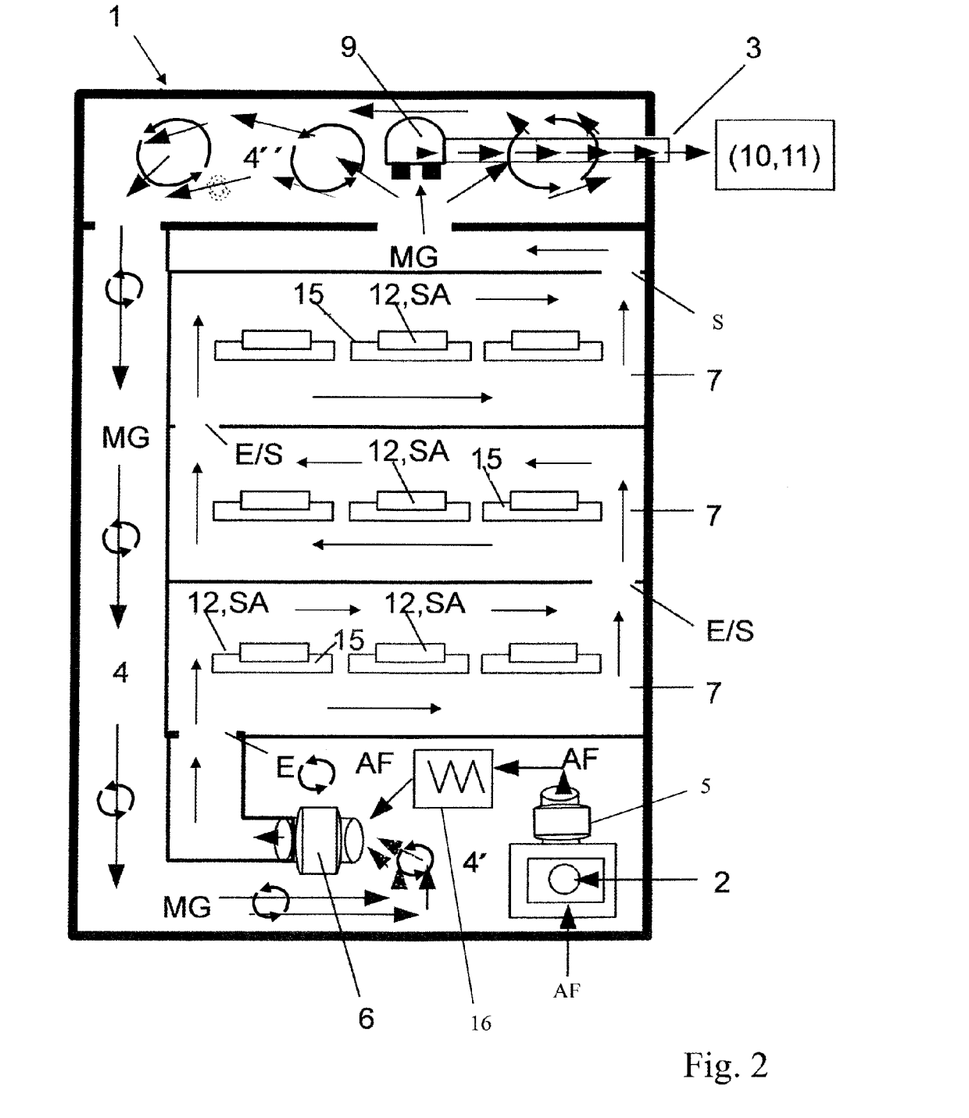
FIG. 2 shows, in a diagrammatic and simplified way, a side-elevation cutaway of a second embodiment of a device according to the invention.
Figure 3:
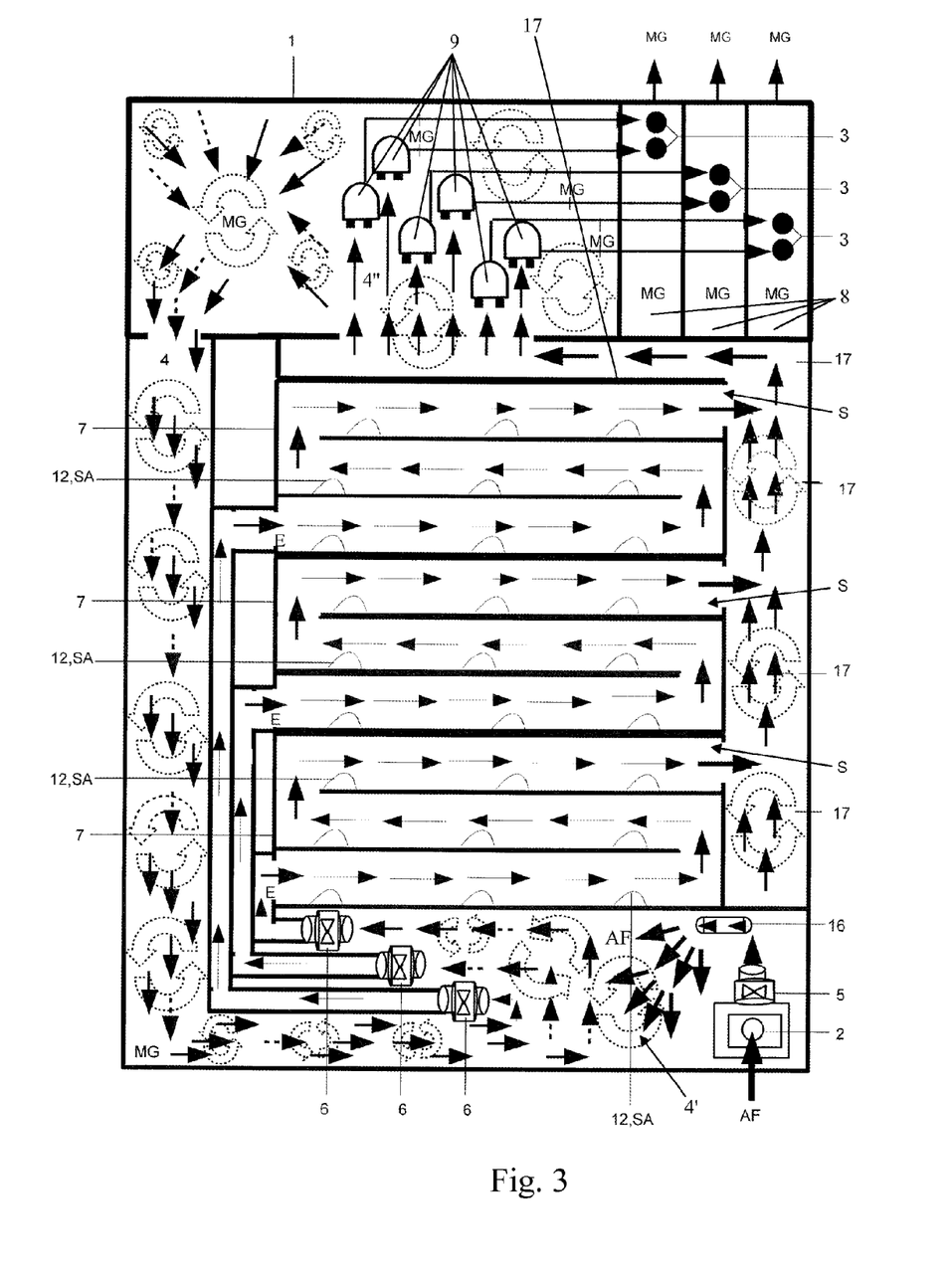
FIG. 3 shows, in a diagrammatic and simplified way, a side-elevation cutaway of a third embodiment of a device according to the invention.

By referring to FIGS. 1 to 3 referred to above, this invention therefore has as its object a method for enriching, preferably saturating, ordinary air with active substances SA that are present in gaseous phase, in particular with volatile substances for deodorizing, perfuming, disinfecting and/or insect control, wherein it essentially consists in implementing, in an essentially airtight chamber 1, the following operations:

a) Introducing gaseous fresh air AF that is not laden with active substances into said chamber 1, b) Introducing it via at least one inlet E into at least one enrichment or saturation chamber 7 for bringing said fresh air AF into contact with at least one volatile active substance SA that is present in the gaseous phase so as to enrich it, preferably until it is saturated, with said volatile active substance(s) SA, c) Drawing off, at the outlet S of said enrichment or saturation chamber(s) 7, a portion of the gas mixture MG that is enriched at a level that is sufficient or saturated at the end of stage b) for the purpose of its storage in an internal storage chamber 8 or its draining toward the outside via one or more outlet openings 3 of said chamber 1, d) Reinjecting the portion of gas mixture MG that is not drawn off in stage c) or all of said enriched or saturated gas mixture MG into said at least one enrichment or saturation chamber 7 so as to increase the enrichment level of said gas mixture MG, keeping it at its maximum saturation level or reducing it by mixing it, in this case, before it is introduced into said at least one enrichment or saturation chamber 7 with the new non-laden fresh air AF that is introduced from the outside into said chamber 1.

The method according to the invention therefore makes it possible to manufacture, starting from ordinary air, either normal atmospheric air, i.e., starting from natural air that is sufficiently clean and healthy and therefore sufficiently free of atmospheric pollutants that may or may not have a smell (industrial or natural), pathogenic germs or insects that are carriers of such germs, treatment air that is particularly laden with or rich in active substances intended for deodorizing, perfuming, disinfecting and/or insect control treatment for the purpose of treating foul-smelling and/or polluted air. This air that is sufficiently pure to be usable within the framework of this invention can be drawn off in situ or can come from suitable storage tanks, for example of pressurized air.

In contrast, any impure or polluted air that requires a purification, deodorizing and/or decontamination (purifying) treatment will be termed "polluted."

Within the framework of this invention, "fresh air" is defined as the outside air in the method or device according to the invention that is not laden with active substances and whose quality or degree of purity is sufficient to be able to be used.

Owing to the method according to the invention, the laden air that is obtained can be so enriched, and even saturated with active substances, that the effectiveness of the method for purification of the polluted air per se is considerably improved, both on the technical level (reduced treatment times, qualitatively better results) and on the economic level (reduced costs for installation, treatment and maintenance).

As active substances SA that should be present in the gaseous phase, in particular the volatile substances for deodorizing, perfuming, disinfecting and/or insect control that are conventionally used and known to one skilled in the art will be used, with the latter comprising both scented substances that simply mask (in particular by superposition or saturation) the objectionable odors as well as the chemically and/or physically reactive substances that act on the foul-smelling molecules and/or undesirable organisms for neutralizing them and even destroying them, for example by modification, decomposition or physical or chemical deactivation.

By way of nonlimiting examples of active substances, in particular the chemical families of aldehydes, terpenes, esters, insecticides, biocides, deodorizers, and other known compounds, such as those cited in, for example, the application EP-A-1 334 735, will be cited.

Bringing into contact, inside the enrichment or saturation chamber(s) 7, gaseous fresh air AF with the volatile active substances SA makes it possible to enrich said fresh air AF with said active substances until obtaining a gas mixture MG that is sufficiently concentrated, and even saturated, with said substances SA. This bringing into contact or exchange in the gaseous phase is done by making the gaseous fresh air AF pass over a surface 12 of two-dimensional exchange (for example, a surface plate coated with a layer of active substance SA) or of three-dimensional exchange of a volumetric support (for example, a porous ceramic volumetric body) laden with active substances SA from which the latter can be freed, for example by circulation, evaporation, entrainment, or the like.

This circulation phenomenon can be promoted or controlled in particular by the selection of particularly volatile active substances SA, by increasing the temperature of the gases taking part in the exchange, by increasing the exchange active surface, by using the fresh air AF that carries little or no burden, by increasing the pressure (the stream) with which the fresh air AF that is not laden or the gas mixture MG that is already partially laden with substances passes over the surfaces or volumetric supports that are laden and enters into contact with said active substances SA, or by combining several of the above-mentioned measures.

As modules that are laden with active substances SA that are suitable for this invention, it is possible to cite, for example, cassettes in the form of plates marketed under the name "AIR FORCE" by the Biothys Company GmbH at Willstädt in Germany. These ready-to-use cassettes essentially consist of plates of active substances that are captured (in a releasable way) in a gel.

At the outlet S of the enrichment or saturation chamber(s) 7, i.e., at the end of the enrichment or saturation circuit through which the non-laden fresh air AF will have passed (when it enters said circuit for the first time) or the enriched gas mixture MG or (when the air that was already enriched above was reinjected into the circuit), a portion of said sufficiently enriched (or saturated) gas mixture MG is drawn off, if this is possible and desired, so as to store it, preferably under pressure, for the purpose of creating a reserve of ready-to-use treatment air in an internal storage chamber 8 or an external storage tank 11 or so as to send it to a consumer 10 where it can be used directly, for example for deodorizing a site. Said internal storage chamber(s) 8 will advantageously be produced in such a way as to occupy a total volume that can typically range from 100 l to 1,000 l, and will be designed to withstand a pressure of several bar (typically up to 15 bar). In a preferred way, each h and [sic] equipped with a non-return plug or valve 14 as suggested by way of example in FIG. 2 for preventing any reflux into the second zone 4" of the chamber 1.

Advantageously, drawing off the entire formed gas mixture MG, at least temporarily, will be prevented so as to allow the recirculation of gases in the enrichment or saturation circuit that is installed inside the chamber 1.

Actually, the portion of gas mixture MG that is not drawn off in stage c) or the entirety of said enriched or saturated gas mixture MG is reinjected into said at least one enrichment or saturation chamber 7 so as to increase again the level of enrichment of said gas mixture MG, to keep it at its maximum saturation level already attained, or to reduce it by mixing it, in this case, before its introduction into said at least one enrichment or saturation chamber 7 with the new non-laden fresh air AF that is introduced from the outside into said chamber 1.

According to an advantageous characteristic, the method according to the invention is characterized in that the gaseous fresh air AF that is not laden with active substances SA is introduced into said chamber 1 by suction, preferably by being filtered, by means of at least one first suction device, preferably by means of a first fan 5 at at least one inlet opening 2 of said chamber 1.

Other means that are well known to one skilled in the art can also be used as suction means, for example pumps. However, the use of fans proves more convenient and more economical and is therefore preferred. The use of suitable filters makes it possible to prevent the suction of undesirable objects such as foreign bodies, sand, dust, pollen, grasses, insects and the like that run the risk of hindering the proper operation of the installation. Additional physical and/or chemical filters can also be used if the air that they use is not sufficiently pure or clean.

In a particularly advantageous manner, the temperature of the incoming non-laden fresh air AF and/or the temperature of the gas mixture MG inside the chamber 1 is adjusted by means of a heating and regulating device and preferably maintained at approximately 25° C.

Thus, an operation, in particular a gas exchange between the gases and the volatilized active substances that is as constant and high-performing as possible, is ensured.

A regulation of the temperature is particularly useful and recommended when the method is implemented in a variable climatic environment, for example in regions where the temperature varies a lot over the time the method is implemented, for example over the course of a day or at the mercy of the seasons.

As mentioned above, the method according to the invention is again characterized in that the gaseous contact, in at least one enrichment or saturation chamber 7, of said gaseous fresh air AF with said at least one active substance SA that is volatile in the gaseous phase so as to enrich said fresh air AF, preferably until it is saturated, in said active substance(s) SA that is/are volatile in the gaseous phase, is done by making said fresh air AF or the reinjected gas mixture MG of stage d) circulate on, under and/or along one or more laden surfaces 12 and/or through at least one volumetric body that is laden with one or more volatile active substances SA for deodorizing, perfuming, disinfecting and/or insect control and that thus circulate, in gaseous form, for enriching or saturating said fresh air AF or the reinjected gas mixture MG.

The quality of the gas exchange between the fresh air AF or the gas mixture MG that is already enriched with the active substance(s) SA influences the effectiveness of the treatment air production and is therefore to be the best possible. As already indicated, the increase of the effective exchange surface area makes it possible to optimize this exchange. Attention will therefore be paid to guaranteeing a contact between the different gases that is as significant as possible by ensuring that the gases to be enriched duly pass over the surfaces 12 to be best laden with active materials SA or that they duly pass through the latter, in the case of volumetric bodies, by being duly impregnated and carrying said substances in the streams thereof.

Advantageously, it is possible to provide that said surface(s) 12 and/or the volumetric bodies passed through are heated directly or indirectly in an adjustable manner by means of an adjustable heating device so as to regulate the amount of volatile active substance SA that is circulated or drawn off per unit of time and surface area.

It will be possible to use all conventional adjusting devices and mechanisms known to one skilled in the art that make it possible to adjust automatically a temperature value that is measured at a predefined setting for the purpose of obtaining a certain release of active substance(s) SA per unit of time and surface area or expressed in terms of mass of active substance(s) released from its surface support (laden gel plates) or volumetric support (laden porous body) per hour. One skilled in the art will know how in particular to determine without difficulty the amount of active substance(s) SA to release to obtain a given content for a defined gas stream.

According to another characteristic, the drawing-off, at the at least one outlet S of said enrichment or saturation chamber(s) 7, of a portion of enriched gas mixture MG is done by suction by means of one or more suction devices, preferably by means of one or more compressors 9.

Other means that are well-known to one skilled in the art can also be used as suction means, for example pumps. However, the use of compressors proves better-performing since the ready-to-use treatment air is generally compressed for the purpose of its storage or its routing to its place of use and is therefore preferred.

In a preferred way, the drawing-off from stage c) is done when the enrichment of gas mixture MG in the active substance SA in the gaseous phase in question is greater than or equal to 50%, preferably greater than or equal to 70%, and more preferably greater than or equal to 95% of the theoretical maximum level of saturation of air in said active substance SA.

Thus, treatment gases with different contents of active substances SA but whose concentration is advantageously relatively—and even much—larger than that of the gases obtained with methods or devices according to the state of the art are obtained, with the latter conventionally having contents of active substances on the order of several % of the theoretical maximum level of the saturation of air in said active substance SA.

According to another characteristic, the method according to the invention is noteworthy in that the ratio between the stream of incoming non-laden gaseous fresh air AF and the stream(s) of enriched or saturated gas mixture MG exiting from the chamber 1 is greater than 1.5, preferably between 1.5 and 4, and more preferably between 4 and 8.

This stream difference that is created by adjusting the operational parameters (power, flow rate . . . ) of the air suction means at the input(s) 2 of the outlet(s) 3 of the chamber 1 makes it possible to keep the gases circulating in the enrichment or saturation circuit inside the pressurized chamber 1 in such a way as to promote the extraction of active substances SA in the chambers 7 and the homogeneity of the gas mixtures that are obtained, in particular at the inlet of non-laden gaseous fresh air AF.

As for the suction at the inlet 2, the reinjection of the stage d) of the gas mixture MG that is enriched or saturated with the new non-laden gaseous fresh air AF is advantageously implemented by means of at least one second suction device, preferably by means of a second fan 6.

So as to be able to control the method and to adapt it to the needs of the user, it is provided to regulate the gas stream generated by the at least first and/or second suction device, preferably the first and/or second fan 5, 6, so as to control the amount of volatile active substance SA that is circulated or drawn off per unit of time and surface area.

According to a particular embodiment, the introduction of non-laden gaseous fresh air AF is done continuously during the entire enrichment or saturation cycle.

It is also possible to provide a mode where the intake of non-laden gaseous fresh air AF is interrupted for a portion of the enrichment or saturation cycle, in particular when a desired specific content is reached, for example a maximum content of saturation, and where the capacity of the installation has sufficiently produced saturated gas mixture MG for meeting the requirements during the given interruption period. The supply of fresh air AF will then be able to resume as soon as the stocks no longer suffice and as soon as it is necessary to restart the production of saturated treatment gas mixture.

Advantageously, the amount and/or the time of introduction of non-laden gaseous fresh air AF and/or drawing-off of the enriched or saturated gas mixture MG are programmable, for example by means of any conventional system of timing and actuation known to one skilled in the art. It thus is possible to meet demands varying over time or to preprogram production/stopping phases when a particularly large amount of gas mixture is to be produced or when the method is to be stopped, for example for the sake of maintenance.

The invention also has as its object a device for implementing the method. In relation to FIG. 1 or 2 that show two examples of devices according to the invention, it is possible to see that such a device is characterized in that it essentially comprises an essentially airtight chamber 1, equipped with at least one inlet opening 2 and at least one outlet opening 3, linking both with the outside of said chamber 1, a main compartment 4 that is supplied—at a first zone 4' of the latter via said at least one opening 2—with outside fresh air AF that is not laden with active substances SA by means of at least one first suction device, preferably at least one first fan 5, and equipped, within itself, with at least one second suction device, preferably at least one second fan 6 drawing in the gases contained in said main compartment 4 toward at least one inlet E of at least one chamber 7 for enrichment or saturation of said gases with volatile active substances SA, with the outlet(s) S of the enrichment or saturation chamber(s) 7 emptying into a second zone 4" of said main compartment 4 that is geographically removed from said first zone 4' and inlet opening(s) 2 and that is equipped, within itself, with at least one compressor 9 for drawing off at least a portion of the enriched or saturated gas mixture MG that is formed, intended for an internal storage chamber 8, an external consumer 10 or an external intermediate storage tank 11 via the at least one outlet opening 3, with said second zone 4" being in gaseous communication with said first zone 4' in such a way as to make possible a reinjection of the enriched or saturated gas mixture MG formed in the at least one enrichment or saturation chamber 7, if necessary with non-laden fresh air AF that comes in via the inlet opening(s) 2.

"Geographically removed" is defined as the fact that the second zone 4" is sufficiently distant from the first zone 4' and inlet openings 2 so as not to disrupt the proper operation of the device.

In the example shown in the above-mentioned figures, a chamber 1 that is equipped with a single inlet and a single outlet is shown. Such a chamber 1 can be an essentially airtight cabinet made of steel, for example stainless steel or aluminum, whose dimensions are naturally adapted to the amount of gas mixture MG that should be produced. By way of concrete example, a small chamber 1 will measure approximately 2 meters in height for a width and a depth that are also approximately 2 m, i.e., a rough volume of 8 m$^3$.

The inlet opening 2 and the outlet opening 3 are equipped with ad hoc seals (not shown) so as to prevent or to minimize at a maximum any leakage of gas mixture MG toward the outside.

The fresh air AF (free of any active substance SA) that is outside and of sufficient quality is drawn in through the inlet opening 2 via the suction means produced here in the form of a first fan 5 that can be equipped with a filter (not shown), for example, an insect filter, a sand filter, a particle filter, . . . .

The inlet opening 2 is preferably located in the low part of the chamber 1 that is close to the ground on which it rests.

According to another characteristic, the device according to the invention comprises at least one means for heating and regulating the temperature of the outside fresh air AF that is not laden with active substances SA and/or gases already present in the main compartment 4. As shown, the gaseous fresh air AF that thus penetrates the chamber 1, at the first zone 4', passes over or close to an adjustable radiator 16, for example of 500 W at 230 V/50 Hz, which heats, if necessary, up to the desired temperature, for example 25° C. Other adjustable radiators (not shown) can be provided as means for heating and regulating gases circulating inside the chamber 1 for optimizing the mixtures and the release of active substances SA deposited on the surfaces 12 or imprisoned in the laden volumetric bodies.

For the sake of clarity, and unless otherwise indicated, the electrical connections, in particular for supply, the temperature sensors or probes, the regulating means, the control and management electronics of the device, and the valves and sealing joints, etc., have not been or have not all been shown in the figures that are of the simplified schematic diagrams, with one skilled in the art knowing by himself how to execute any conventional constructive measure that proves necessary.

The fresh air AF that is thus brought to the proper temperature is drawn in, always at the low part of the chamber 1, through a second suction device provided here in the form of a second fan 6. By way of indication, the first and second fans each have a normal operating flow rate on the order of 170 m$^3$/h for a power on the order of 40 W at 230 V/50 Hz.

In the first zone 4', close to the inlet of said fan 6, non-laden fresh air mixes normally, after a certain time of operation of the device, with the already formed gas mixture MG (i.e., the fresh air AF that has already passed through an enrichment or saturation chamber and that is already laden with active substances SA) and therefore coming, under the action of the suction, from the second zone 4" of the compartment 4 located in the top part of the chamber 1 at the outlet S of the enrichment or saturation chamber(s) 7.

The thus formed gas mixture MG supplies, via a dedicated pipe, a first independent enrichment or saturation chamber 7 in which it penetrates via an inlet E, which it passes through in a direction that is essentially horizontal from left to right in FIG. 1 over a distance that corresponds roughly to the width of the device or the chamber 1 for getting back to an elbow and passing through again, from the right to the left, a second compartment that is similar to the first that it passes through for thus leaving said chamber at an outlet S to which a second new enrichment or saturation chamber 7 can be connected immediately, and which can also in its turn be extended from a third new enrichment or saturation chamber 7 of the same type, etc.

In the example shown in FIG. 1, it is thus possible to identify five enrichment or saturation chambers 7 that come after one another in a series, the last outlet S then being located in the top part of the chamber 1 at the second zone 4" where the volume of gas mixture MG produced can, when it is sufficiently enriched or saturated, be drawn off by the compressor 9 and stored in the internal storage chamber 8 or can leave the chamber via the outlet opening 3.

In the example that is shown in FIG. 2, these are three enrichment or saturation chambers 7 that come after one another in a series, the last outlet S also being located in the top part of the chamber 1 at the second zone 4". In this example, said chambers 7 have only one compartment that the stream of gas mixture MG passes through only once before penetrating the following chamber. It will be noted that the direction of the gas stream from the left to the right for the first chamber is reversed during the passage of the following chamber and that the path traveled by said gas mixture MG along an enrichment or saturation chamber 7 roughly corresponds to the width of the chamber 1.

These illustrative examples show how to take advantage of the overall volume of the chamber 1 for increasing and optimizing the length of the path traveled by the gas mixture and therefore the time of contact of the different gases with the surfaces 12 and/or volumetric bodies laden with active substances that they sweep or pass through to enrich them until they are saturated with the active substance(s). Actually, during their passage through the enrichment or saturation chambers 7, the fresh air AF that is not yet laden and/or the gas mixture already enriched in advance by a first passage enters into contact with the volatile active substances SA and is more or less laden with the latter, in particular based on the nature of the active substances SA, the gas to be enriched, the time of contact, the temperature, the degree of saturation of the gas that is present . . . .

The degree of enrichment or saturation of the gas mixture MG exiting from the (last) enrichment or saturation chamber 7 can be measured by drawing-off, by means of a suitable probe placed in the chamber, or evaluated empirically. If the content of active substances SA is not sufficient, the gas mixture MG will not be drawn off by the compressor 9 and will continue its path automatically into the compartment 4 toward the first zone 4', drawn in by the second fan 6 as shown diagrammatically in the left part of FIG. 1 or 2. There, it will be mixed, if necessary, with the new fresh air AF or it will be drawn in again into the pipe that leads to the first enrichment or saturation chamber 7 for a new passage. The cycle thus resumes until a gas mixture MG is obtained whose enrichment level is satisfactory.

By way of information, the compressor 9 has, in a normal operating mode, a flow rate on the order of only 16 m$^3$/h for a power on the order of 210 W at 230 V/50 Hz, whereas the first and second fans 5, 6 each have a normal operating flow rate on the order of 170 m³/h.

As mentioned above, the device according to this invention is characterized in that the enrichment or saturation chamber(s) 7 comprise(s) at least one laden surface 12 and/or at least one volumetric body that is laden with volatile active substance(s) SA for deodorizing, perfuming, disinfecting and/or insect control, in such a way as to be able to circulate, in gaseous form, for enriching or saturating said fresh air AF or the reinjected gas mixture MG.

According to the embodiment shown in FIGS. 1 and 2, the enrichment or saturation chambers 7 are made in the form of airtight containers of an overall elongated shape inside of which are arranged the surface(s) 12 laden with active substance(s) SA distributed over essentially the entire longitudinal range of said containers, preferably over at least two parallel levels 13, 13' that are flat and offset from one another in terms of height (FIG. 1).

"Overall elongated shaped" is defined as a container shape whose cross-section or width has a smaller size than that of the length of said container.

The active substance(s) SA in particular can be deposited as suggested diagrammatically on the surface(s) 12, for example in the form of mounds of isolated material, deposited coated gel plates, layers of applied active substances or the like. The surfaces 12 can be the walls of enrichment or saturation chambers 7 per se or connected to the latter. The surface(s) 12 that are laden, for example with fine plates of impregnated gel, and/or the volumetric bodies laden with active substances SA, for example, porous bodies made of ceramic or zeolites, can also be deposited on supports 15, made, for example, in the form of slidable drawers or shelves, mounted inside each enrichment or saturation chamber 7 as FIG. 2 shows, in such a way as to leave a large enough space between said surfaces 12 or volumetric body and the walls of said chamber so that the gas streams can flush them effectively and thus make possible the release and the entrainment of said active substances SA. Advantageously, the supports 15 are made so as to allow an optimum access of gases to the active substances SA, in particular by providing a sufficient number of openings there. Said supports 15 can thus be made in the form of grids, threads or mesh ensuring a good gas-active substances SA contact. The exchange, the replacement, or the resupplying of active substances SA of said supports 15 is also facilitated when the latter are made in the form of slidable drawers that have easy access and that can be easily manipulated.

So that the circulation of the air or the gas mixture is sufficient, a spacing of at least 5 mm can be provided, for example, between two parallel gel plates of the "AIR FORCE" type mentioned above.

Advantageously, the enrichment or saturation chamber(s) 7 have baffles. This also makes it possible to increase the dwell time of gases in said enrichment or saturation chambers 7.

According to a variant that is not shown, the enrichment or saturation chamber(s) 7 has/have adjustable heating means of laden surfaces 12 and/or volumetric bodies laden with active substance(s) SA.

This heating makes it possible to improve and/or to control the release or circulation of liquid or solid active substances SA in the gas mixture that has to be enriched or saturated. It can be done in a direct manner, for example by directly heating the active substances SA, for example by heating their support or container that contains them or indirectly by heating the direct environment of said active substances SA that will then transmit the heat thereof to the above-mentioned supports and/or active substances.

This heating can be done in particular by a radiator that is placed close to the active substances SA to be heated, in particular by a radiator that is designed to heat air or the gas mixture MG that is to be enriched. It is also possible to provide for heating the laden gel plates directly, for example by heating the supports or metal surfaces on which they rest or into which they are inserted.

According to a third embodiment shown in FIG. 3, the device according to this invention is characterized in that it has several (three) second fans 6, each being connected to an enrichment or saturation chamber 7 that is specific thereto by a pipe, each enrichment or saturation chamber 7 having its own outlet S emptying into or connected to, by means here of a collecting pipe 17, said second zone 4" that is equipped with at least one compressor 9 for sampling at least one portion of the enriched or saturated gas mixture MG, and an element for control and management of said several second fans 6 and said compressor(s) 9. Said drawn-off mixture is drained from the chamber 1 by the six compressors 9 via the six outlet openings 3.

It is necessary to ensure that the flows or streams generated by said second fans remain higher than those accumulated by the compressors 9 in such a way that excessive pressure always prevails inside the chamber 1. This excessive pressure makes possible a better release of the active substances SA and a good mixture and a good recirculation of the gases inside said chamber 1. In the example of FIG. 3, the maximum sum of the streams drawn in by the six compressors 9 is 9×16=96 m³/h per 170 m³/h of the stream coming from the outside (fresh air AF) or the stream of gas mixture MG and optionally fresh air AF drawn in by each fan 6 with a capacity that is identical or equal to that of the first fan 5.

Of course, all of the possible combinations are conceivable by one skilled in the art relative to the implementation of the device according to the invention at the enrichment or saturation chambers 7 that can be arranged in a series one after the next and/or parallel one beside the other. One skilled in the art will know to provide means for connection and supply and extraction that are suitable for the circulating gases in such a way as to create the recirculation circuit that is suitable for this invention that makes it possible during successive shifts of gases to enrich them or to saturate them with active substances SA before they are drawn off to be stored or used in the treatment of foul-smelling and/or infested atmospheres.

The effective number of recirculations of the gas inside the chamber 1, i.e., the number of shifts of the gas mixture MG into the enrichment or saturation chamber(s) 7 obviously depends on numerous parameters and in particular on the degree of saturation of active substances SA that it is desired to obtain. By way of example, the gas mixture MG may have to perform 30 shifts before reaching a content of 100% of the theoretical maximum attainable in quantity of laden active substances SA. A consumption of active substances SA of 3 g/h is indicated as a point of reference.

This invention also has as its object the use of the method according to the invention characterized in that the enriched or saturated gas mixture MG that is obtained by the implementation of said method is mixed, according to an effective amount, with the polluted air that is to be treated for deodorizing it, perfuming it, purifying it and/or removing from it the insects (flies, mosquitoes, . . . ) that it contains.

"Effective amount" is defined as an amount that is sufficient for deodorizing, perfuming, purifying and/or decontaminating the polluted air, either completely or according to the desired degree and/or based on the application considered.

One skilled in the art will know how to adapt, for example according to the so-called trial-and-error method, the amounts of air to be treated and of gas mixture MG, in particular based on the degree of pollution of said air and the concentration of active substances of the gas mixture MG.

By way of nonlimiting examples of atmospheres or environments that can be treated, it is possible to cite:

The industrial smokestacks,
The installations for production of natural gas,
The garbage dumps, recycling centers or composting centers,
The sewers and sewer networks,
Sewage treatment plants, in particular the settling basins,
The industrial sites that produce objectionable odors or strong and bothersome odors (paper industry, chemical industry, slaughterhouses, industrial animal breeding farms, fish canneries . . . ),
More or less confined public atmospheres to be scented (stores, meeting rooms, theaters, train stations or airports, trains, airplanes, metro corridors . . . ) or to be deodorized (restaurants, service stations, athletic locker rooms, . . . ), and
The natural sites that have a particularly strong smell (marshes, stagnant water, . . . ).

The technology according to the invention is also particularly useful for treating so-called "ATEX" (explosive atmospheres) zones by installing a device according to the invention outside of this zone and by providing suitable sheaths or pipes that make it possible to supply said zones with the gas mixture MG for the treatment of their atmospheres. The device according to the invention can be installed in the immediate proximity of said zones or at great distances from the latter (300 m to several kilometers), which [is] in fact a particularly flexible and practical tool. This also makes it possible to centralize the devices for manufacturing the treating gas mixture MG, which can then be distributed using an ad hoc piping network. Such a distribution is also particularly advantageous when it is a matter of treating, not a small zone localized in a compact way (for example, the well-defined internal air volume of an industrial animal breeding shed) but the entire network of volumes extending in a linear and/or branched way, such as in particular a network of sewers or subterranean corridors. In this latter case, the sheaths or pipes conveying the gas mixture MG can be equipped, for example at regular intervals, with circulation means (openings, nozzles, fans, . . . ), preferably adjustable and/or programmable, of said gas mixture MG in the environment that is to be treated.

Of course, the invention is not limited to the embodiments described. Modifications are possible, in particular from the standpoint of the composition of the various elements or by substitution of equivalent techniques, without thereby exceeding the field of protection of the invention as defined by the claims.

The invention claimed is:

1. A method for enriching or saturating ordinary atmospheric air, called fresh air (AF), with active substances (SA) that are present in gaseous phase, with volatile substances for deodorizing, perfuming, disinfecting and/or insect control, comprising implementing, in an airtight chamber (1), the following operations:

a) Introducing a stream of gaseous fresh air (AF) that is not laden with active substances into said chamber (1) by means of a first fan (5) at least one inlet opening (2) of said chamber (1),
b) Introducing said fresh air (AF) via at least one inlet (E) into several enrichment or saturation chambers (7) for bringing said fresh air (AF) into contact with at least one volatile active substance (SA) that is present in the gaseous phase so as to enrich said fresh air (AF) with said at least one volatile active substance (SA) to form a gas mixture (MG) that is enriched at a level that is sufficient or saturated,
c) Drawing off, at the outlet (S) of said enrichment or saturation chambers (7), a portion of the gas mixture (MG) that is enriched at a level that is sufficient or saturated at the end of stage b), by means of one or more compressor(s) (9), for the purpose of storing the gas mixture (MG)in an internal storage chamber (8) or draining one or more streams of gas mixture (MG) toward the outside via one or more outlet openings (3) of said chamber (1),
d) Reinjecting the portion of the gas mixture (MG) that is not drawn off in stage c) or all of said enriched or saturated gas mixture (MG) into said enrichment or saturation chambers (7) by means of a second fan (6) so as to increase the enrichment level of said gas mixture (MG), keeping said gas mixture (MG) at a maximum saturation level or reducing the enrichment level of said gas mixture (MG) by mixing said gas mixture (MG), in this case, before said gas mixture (MG) is introduced into said enrichment or saturation chambers (7) with the new non-laden fresh air (AF) that is introduced from the outside into said chamber (1), with the ratio between the stream of incoming non-laden gaseous fresh air (AF) and the stream(s) of the enriched or saturated gas mixture (MG) exiting from the chamber (1) being greater than 1.5, and
e) Regulating the gas stream generated by the first and/or second fan (5, 6) so as to control the amount of volatile active substance (SA) that is circulated or drawn off per unit of time and surface area.

2. The method according to claim 1, wherein the gaseous fresh air (AF) that is not laden with active substances is introduced into said chamber (1) by being filtered.

3. The method according to claim 1, wherein the temperature of the incoming non-laden fresh air (AF) and/or the temperature of the gas mixture (MG) is adjusted by means of a heating and regulating device and maintained at approximately 25° C.

4. The method according to claim 1, wherein the bringing into gaseous contact, in the enrichment or saturation chambers (7), of said gaseous fresh air (AF) with said at least one volatile active substance (SA) in the gaseous phase so as to enrich said fresh air (AF), until said fresh air (AF) is saturated, in said volatile active substance(s) (SA) in gaseous phase, is done by making said fresh air (AF) or the reinjected gas mixture (MG) of stage d) circulate in, under and/or along one or more surfaces (12) and/or through at least one volumetric body that is/are laden with at least one volatile active substances (SA) for deodorizing, perfuming, disinfecting and/or insect control and that thus circulate, in gaseous form, for enriching or saturating said fresh air (AF) or the reinjected gas mixture (MG).

5. The method according to claim 4, wherein said surface(s) (12) and/or the at least one volumetric body is /are heated directly or indirectly in an adjustable way by means of an adjustable heating device so as to regulate the amount of volatile active substance (SA) that is circulated or drawn off per unit of time and surface area.

6. The method according to claim 1, wherein the drawing-off of stage c) is done when the enrichment of the gas mixture (MG) in the active substance (SA) in the gaseous phase in question is greater than or equal to 50% of the theoretical maximum level of saturation of the air in said active substance (SA).

7. The method according to claim 1, wherein the ratio between the stream of incoming non-laden gaseous fresh air (AF) and the stream or streams of enriched or saturated gas mixture (MG) exiting from the chamber (1) is either between 1.5 and 4 or between 4 and 8.

8. The method according to claim 1, wherein the introduction of non-laden gaseous fresh air (AF) is done continuously during the entire enrichment or saturation cycle.

9. A device for implementing the method according to claim 1, comprising an airtight chamber (1), equipped with at least one inlet opening (2) and at least one outlet opening (3) linking both with the outside of said chamber (1), a main compartment (4) that is supplied —at a first zone (4') of said chamber (1) —by said at least one opening (2) with outside fresh air (AF) that is not laden with active substances (SA) by means of at least one first fan (5), and equipped, within said chamber (1), with at least one second fan (6) that draws in the gases that are contained in said main compartment (4) to at least one inlet (E) of several enrichment or saturation chambers (7) of said gases in volatile active substances (SA), with the outlet(s) (S) of said enrichment or saturation chamber(s) (7) emptying into or connected to a second zone (4") of said main compartment (4) that is geographically removed from said first zone (4') and inlet opening(s) (2) and that is equipped, within said chamber (1), with at least one compressor (9) for drawing off at least a portion of enriched or saturated gas mixture (MG) that is formed, headed for an internal storage chamber (8), an external consumer (10) or an external intermediate storage tank (11) via the at least one outlet opening (3), with said second zone (4") being in gaseous communication with said first zone (4') in such a way as to make it possible to reinject the enriched or saturated gas mixture (MG) formed into said enrichment or saturation chambers (7), if necessary with the non-laden fresh air (AF) entering through the inlet opening(s) (2), and wherein said chamber (1) has a means for regulating the gas stream generated by said at least first and/or said at least second fan (5, 6).

10. The device according to claim 9, further comprising at least one means for heating and regulating the temperature of the outside fresh air (AF) that is not laden with active substances (SA) and/or gases already present in the main compartment (4).

11. A device according to claim 9, wherein one or more of said enrichment or saturation chamber(s) (7) comprise(s) at least one laden surface (12) and/or at least one volumetric body that is laden with volatile active substance(s) (SA) for deodorizing, perfuming, disinfecting and/or insect control, in such a way as to be able to circulate, in gaseous form, for enriching or saturating said fresh air (AF) or the reinjected gas mixture (MG).

12. The device according to claim 11, wherein one or more of said enrichment or saturation chamber(s) (7) is/are produced in the form of airtight containers with an overall elongated shape inside of which are placed the surface(s) (12) and/or the at least one volumetric body that is/are laden with active substance(s) (SA) distributed over essentially the entire longitudinal range of said containers, preferably on at least two parallel levels (13, 13') that are flat and offset from one another in terms of height.

13. The device according to claim 11, wherein one or more of said enrichment or saturation chamber(s) (7) have baffles.

14. The device according to claim 11, wherein one or more of said enrichment or saturation chamber(s) (7) has/have adjustable heating means of surfaces (12) or volumetric bodies that are laden with active substance(s) (SA).

15. The device according to claim 9, wherein it has several second fans (6), with each being connected to an enrichment or saturation chamber (7) that is specific thereto, each enrichment or saturation chamber (7) having an outlet (S) emptying into or connected to said second zone (4") equipped with at least one compressor (9) for drawing off at least one portion of enriched or saturated gas mixture (MG), and an element for control and management of said several second fans (6) and said compressor(s) (9).

16. The method according to claim 1, wherein the enriched or saturated gas mixture (MG) that is obtained by implementing said method is mixed, according to an effective amount, with polluted air that is to be treated for deodorizing the polluted air, perfuming the polluted air, purifying the polluted air and/or removing insects from the polluted air.

17. The method according to claim 2, wherein the temperature of the incoming non-laden fresh air (AF) and/or the temperature of the gas mixture (MG) is adjusted by means of a heating and regulating device and preferably maintained at approximately 25° C.

18. The method according to claim 2, wherein the bringing into gaseous contact, in the enrichment or saturation chambers (7), of said gaseous fresh air (AF) with said at least one volatile active substance (SA) in the gaseous phase so as to enrich said fresh air (AF), until said fresh air (AF) is saturated, in said volatile active substance(s) (SA) in gaseous phase, is done by making said fresh air (AF) or the reinjected gas mixture (MG) of stage d) circulate in, under and/or along one or more surfaces (12) and/or through at least one volumetric body that is/are laden with one or more volatile active substances (SA) for deodorizing, perfuming, disinfecting and/or insect control and that thus circulate, in gaseous form, for enriching or saturating said fresh air (AF) or the reinjected gas mixture (MG).

19. The method according to claim 3, wherein the bringing into gaseous contact, in the enrichment or saturation chambers (7), of said gaseous fresh air (AF) with said at least one volatile active substance (SA) in the gaseous phase so as to enrich said fresh air (AF), until said fresh air (AF) is saturated, in said volatile active substance(s) (SA) in gaseous phase, is done by making said fresh air (AF) or the reinjected gas mixture (MG) of stage d) circulate in, under and/or along one or more surfaces (12) and/or through one or more at least one volumetric body that is/are laden with one or more volatile active substances (SA) for deodorizing, perfuming, disinfecting and/or insect control and that thus circulate, in gaseous form, for enriching or saturating said fresh air (AF) or the reinjected gas mixture (MG).

20. The method according to claim 2, wherein the drawing-off of stage c) is done when the enrichment of the gas mixture (MG) in the active substance (SA) in the gaseous phase in question is greater than or equal to 50%, of the theoretical maximum level of saturation of the air in said active substance (SA).

* * * * *